United States Patent
Albert et al.

(10) Patent No.: US 6,773,552 B1
(45) Date of Patent: Aug. 10, 2004

(54) METHOD OF SELECTING AND/OR PROCESSING WOOD ACCORDING TO FIBRE CHARACTERISTICS

(75) Inventors: Denis John Albert, Tokoroa (NZ); John Corrie Fleming Walker, Christchurch (NZ); Ross Lindsay Dickson, North Canterbury (NZ); Thomas Alan Clark, Rotorua (NZ)

(73) Assignee: Carter Holt Harvey Limited, Manukau City (NZ)

( * ) Notice: Subject to any disclaimer, the term of this patent is extended or adjusted under 35 U.S.C. 154(b) by 0 days.

(21) Appl. No.: 09/763,511
(22) PCT Filed: Aug. 24, 1999
(86) PCT No.: PCT/NZ99/00137
§ 371 (c)(1),
(2), (4) Date: May 22, 2001
(87) PCT Pub. No.: WO00/11467
PCT Pub. Date: Mar. 2, 2000

(30) Foreign Application Priority Data

Aug. 24, 1998 (NZ) .............................................. 331527

(51) Int. Cl.⁷ ................................................. D21F 7/06
(52) U.S. Cl. ......................................... 162/263; 162/49
(58) Field of Search ............................. 162/49, 61, 62, 162/198, 259, 263; 73/644, 598, 599, 600, 622, 632, 610, 602, 645, 646, 659, 609, 597

(56) References Cited

U.S. PATENT DOCUMENTS

| 5,013,403 A | * | 5/1991 | Chase .......................... 162/49 |
| 5,760,308 A | * | 6/1998 | Beall et al. ................... 73/644 |
| 5,804,728 A | * | 9/1998 | Beall et al. ................... 73/598 |

* cited by examiner

Primary Examiner—Steve Alvo
(74) Attorney, Agent, or Firm—Hovey Williams LLP

(57) ABSTRACT

The invention provides a method for predictively assessing one or more characteristics of wood pulp produced from solid wood. The method comprises the steps of determining the velocity of sound through the solid wood, and assessing characteristic(s) of wood fiber or wood pulp produced from the wood by reference to the velocity of sound through the solid wood. The method may also comprise the steps of causing a sound wave to be transmitted through the wood, determining the velocity of the sound wave through the wood, and comparing the result to stored information on fiber characteristic(s) versus sound velocity through the wood-type to determine the fiber characteristic(s) for the wood.

4 Claims, 8 Drawing Sheets

METHOD OF SELECTING AND/OR PROCESSING WOOD ACCORDING TO FIBRE CHARACTERISTICS

FIELD OF INVENTION

The invention comprises a method for predictively assessing one or more characteristics of wood fibre or wood pulp produced from wood while the wood is in solid form, such as fibre length or the strength of pulp formed from the wood. The invention has particular application in the selection of wood for pulp and paper or other wood-fibre-based applications such as the production of fibre board.

BACKGROUND OF INVENTION

Optimum segregation of tree stems after felling, or of logs after sawing of the stems into logs, for different applications such as solid or structural grade lumber, manufacture of reconstituted wood products, or pulp and paper manufacture, is an important issue for the forestry and wood products industries because of the variable nature of the raw material and the different properties required in different end products. There are major commercial benefits to be gained by optimising the use of the wood resource for different solid wood, reconstituted, and pulp and paper applications, which may require different properties in the raw material. Differences in the raw material arise due to genetic differences, silvicultural differences, and geographical and site differences. Even within a tree there are differences in wood properties between the corewood of the tree and the outer wood, and also variations from the bottom to the top of the tree, which further complicates the wood segregation issue.

At present, historical wood density information and a general knowledge of trends in fibre properties in different parts of the tree are the only tools available to perform some limited segregation of wood for pulp and paper manufacture for example. Basic density is difficult to measure, and it is correlated with fibre properties only at a population level and so cannot be applied at an individual tree or log level. Little information on wood quality at an individual stand level is available, other than average wood density data from historical measurements, and there is generally no information at all at an individual tree level. To date, basic wood density is the only tool available. Most wood properties are related to the basic density of the wood (ie the amount of dry wood substance per unit volume of wood), but basic density is difficult to measure and impossible to usefully apply at a whole tree level. Density is also a measure of the amount of wood substance and void space in a unit volume of wood, and is not indicative of the number of fibres which make up that space. For example, individual trees can have roughly the same chip basic density, but have very different fibre lengths, fibre width and thickness, fibre wall areas (coarseness), and number of fibres per unit mass of wood.

Some wood segregation on the basis of density is practised in pulp and paper manufacture. High density wood from the outside of the tree (the slabwood) generally has long and coarse (thicker-walled) fibres which are suitable for certain products such as cement-board reinforcing pulp and sack grades. Wood from the top of the tree is more like corewood and has lower density with shorter, thinner walled (low coarseness) fibres. Pulp from this wood is more suitable for printing and writing or tissue grade papers for example. However basic density is still a very crude basis for wood segregation and knowledge of density variability is rather poor.

Softwood kraft pulp qualities are normally determined by the handsheet properties of apparent density or bulk, tensile strength, and out-of-plane tear strength. Fibre length is the critical softwood kraft pulp fibre determinant. With too little fibre length such pulps lose their characteristic softwood reinforcement properties. However, very long, coarse fibres can be difficult to refine and are prone to flocculation and sheet formation becomes a problem. Other fibre properties are also important but only after fibre length requirements are met. Fibre length is critical for the reinforcement properties of softwood kraft pulps. If pulp fibre length falls below a certain critical level of about 2.0–2.1 mm, bulk is abruptly decreased and reinforcement tear/tensile strengths are correspondingly, abruptly lowered.

The Wet Zero Span Tensile (WZST) strength of a pulp is influenced by the number of fibres per unit mass of pulp and by the strength of the individual fibres. Individual fibre strength is in turn influenced by fibre coarseness and intra-fibrewall characteristics such as micro-fibril angle (MFA). WZST strength is a good predictor of Tear Index at a given Tensile Index, the traditional indicator of softwood kraft reinforcement potential.

Pulp quality is very much a function of its end-use. As well as the above mentioned quality factors, end-users of market pulps are also concerned about: ease of beating the amount of energy required to refine a pulp to an acceptable tensile strength; reinforcement potential; and effects on paper sheet formation.

Pulp and paper mills normally utilise the residues from harvesting such as top logs and low grade logs that arise during harvesting operations, and from saw milling such as chips from the slabwood sawn from the outsides of the log.

The measurement of velocity of sound in a log is a non-destructive technique which can be used to evaluate the stiffness of materials by means of sound transmission. The sound wave, for instance induced by the impact of a hammer at one end, travels down the length of a log. The transit time ($\Delta t$) is measured. The modulus of elasticity (MOE) is computed from the transit time and density (p) as follows:

$$MOE = V^2 p = (l/\Delta t)^2 p$$

This is a fundamental relationship for materials. Although a log of wood is not a homogeneous material (compared with an iron bar, for example), and does not obey this law perfectly, relatively good relationships have been found between sound wave speed and the average measured stiffness of lumber which is sawn from the log. U.S. Pat. No. 4,144,669 describes the use of velocity of sound measurement for the grading of wood. Measurements of velocity of sound in a log can be made with industrial stress wave timers, which are commercially available.

SUMMARY OF INVENTION

In broad terms in one aspect the invention comprises a method for predictively assessing one or more characteristics of wood fibre or wood pulp produced from solid wood, comprising determining the velocity of sound through the solid wood, and assessing characteristic(s) of wood fibre or wood pulp produced from the wood by reference to the velocity of sound through the solid wood.

More particularly the method comprises causing a sound wave to be transmitted through the wood, determining the velocity of the sound wave through the wood, and comparing the result to stored information on fibre characteristic(s) versus sound velocity through the wood-type to determine the fibre characteristic(s) for the wood.

In one form the method includes placing a sensing means capable of detecting sound in the wood in contact with or within sensing distance of one end of the length of wood, placing a second sensing means capable of detecting sound in the wood in contact with or within sensing distance of another end of the length of wood, causing a sound wave to be transmitted in the length of wood from one end to the other, detecting the sound at each end of the log or length of wood, determining the velocity of the sound in the wood, and assessing characteristic(s) of wood fibre or wood pulp produced from the wood by reference to stored information on fibre characteristics versus sound velocity through the wood.

In another form the method includes placing means capable of detecting both an original and reflected sound wave in contact with or within sensing distance of one end of the length of wood, causing a sound wave to be transmitted in the length of wood, detecting a reflected echo of the sound in the wood, determining the velocity of the sound in the wood, and assessing characteristics of wood fibre or wood pulp produced from the wood by reference to stored information on fibre characteristics versus sound velocity through the wood.

In broad terms in another aspect the invention comprises apparatus for predictively assessing one or more characteristics of wood fibre or wood pulp produced from solid wood, comprising sensing means capable of detecting the velocity of sound in through the wood, and computer processing means comprising stored information on fibre characteristics versus sound velocity in wood and arranged to determine the fibre characteristic(s) by reference to said stored information on fibre characteristic(s) versus velocity through the wood.

By "sound" is meant normally relatively low frequency energy that will be audible to the human ear eg of the order of 500 to 1000 Hz as will be created by a single impact on a length of wood, by striking the length of wood with a hammer for example. Higher frequencies may be used such as of the order of 15 kHz or above including ultrasound but use of lower frequencies is preferred.

The method and apparatus of the invention may be used with whole stems after felling, logs and sawing of the stems into logs, flitches, cents, or other lengths of lumber or wood in any form, and in this specification and claims "length of wood" is to be understood accordingly.

BRIEF DESCRIPTION OF THE FIGURES

The invention is further described with reference to the accompanying figures in which.

DETAILED DESCRIPTION OF INVENTION

As stated we have found a close correlation between the velocity rate of sound, preferably relatively low frequency sound, through wood and the fibre characteristics of the wood on subsequent fiberising of the wood, in particular the fibre length, and properties of pulp produced using the wood which are dependent on the fibre characteristics of the wood.

In the method of the invention, wood fibre or wood pulp characteristics for wood whole stems, logs, or in other form are predictively assessed by reference to the velocity of sound through the wood. The method involves causing a sound wave to be transmitted through the wood, for example by impacting the wood such as by striking the wood, determining the velocity of sound through the wood, and comparing the result to stored information on fibre characteristics versus sound velocity through the wood-type or species to derive information predictive of the characteristics of wood fibre or pulp produced from the wood. Any device able to determine the velocity of sound including low frequency sound or alternatively higher frequency sound through the wood may be used to measure the time taken for the sound wave to be transmitted through the length of wood from one end to the other. Sound in the wood may be created by impacting the wood with a hammer for example, or by electronic means. The device may comprise one or more sensing heads which contact the wood or are positioned within sensing distance of the wood, such as one or more small microphones spaced from the wood by a foam pad for example. The device may comprise one sensing head at the send end of the length of wood and another at the other (receive) end of the length of wood to sense the time taken for the sound to be transmitted over the length of wood, or a single sensing head at one end of the length of wood which senses the time taken for the sound to be transmitted over the length of wood and reflected back to the same end of the length of wood. The output is fed to computer processing means comprising in memory stored information on fibre characteristics versus velocity of sound through the wood-type or species, and a measure of the fibre or pulp characteristics determined, which may be output as a display on a hand held device, to a memory storage device such as a floppy disc, or to a control system controlling, sorting, chipping, sawing of logs or similar.

Figure 1:
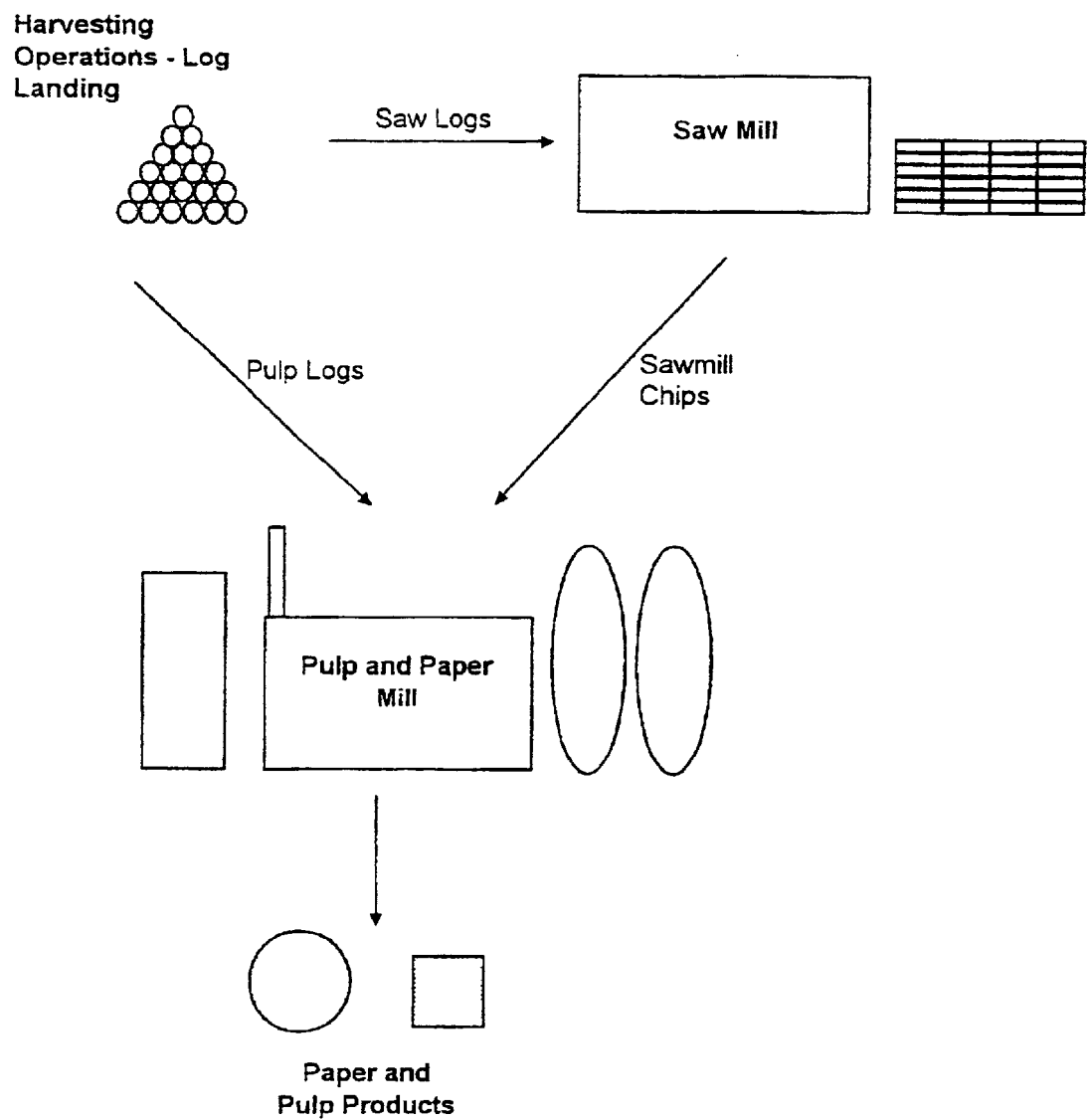
FIG. 1 is a schematic representation of the source of material for a pulp mill.

FIG. 1 is a schematic representation of the source of primary material for a pulp and paper mill. Logs may be assessed as they are received at a pulp and paper mill prior to processing. Alternatively, logging companies may assess whole logs to select whole logs and/or slabwood in the form of sawmill wood chips for subsequent pulping. Results of the data recorded for each log may then be used to determine approximate expected average pulp fibre length and pulp strength characteristics for pulp if formed from that log or slabwood portion of the log by comparison of the data with correlations for velocity of sound with average pulp fibre length or pulp strength.

Logs having velocity of sound characteristics within specified ranges may be identified by an identification means so that each log or the slabwood arising from a sawn log is allocated to a batch for use in the manufacture of a particular pulped product. For example, wood producing pulp having a shorter length weighted average fibre length (LWFL) and a lower WZST strength is preferred for use in the manufacture of very high density papers such as release papers and glassine. High LWFL and WZST strength pulp is most appropriately used for very high tearing strength grades of paper, such as fibre-cement grades. Table 1 shows preferred end-use applications for radiata pine wood producing kraft pulp having specified fibre-length/pulp properties.

TABLE 1

Radiata Pine Kraft Pulp Properties versus End-Use Applications

| Average LWFL (mm) | Coarseness (mg/m) | Fibres/g o.d. pulp (relative) | WZST Strength (km) | Refining Response | End-use (examples) |
|---|---|---|---|---|---|
| 1.80–2.00 | 0.16 | 100 | 10–11 | Beats easily to form high density sheets of relative low tensile strength | Very high density papers e.g. release papers and glassine |
| 2.00–2.20 | 0.18 | 86 | 11–12 | Beats easily to form sheets of high density with moderate tensile strength | Good for reinforcement in products requiring low coarseness fibres, for example in some tissue grades |
| 2.20–2.40 | 0.20 | 69 | 12–14 | Moderately easy to beat forming sheets of intermediate density with good tensile strength | Excellent for reinforcement component of printing and writing grades (fine papers) |
| 2.40–2.60 | 0.23 | 54 | 14–16 | Medium - high coarseness fibres with good tearing strengths; slower beating response | Suitable for manufacture of products which value high tearing strength, such as some packaging grades |
| >2.60 | 0.26 | 44 | 16–17 | Long, coarse fibres that are difficult to refine forming bulky sheets | Very high tearing strength suitable for some speciality grades, such as for fibre-cement board manufacture, and for papers of high bulk |

Figure 2:
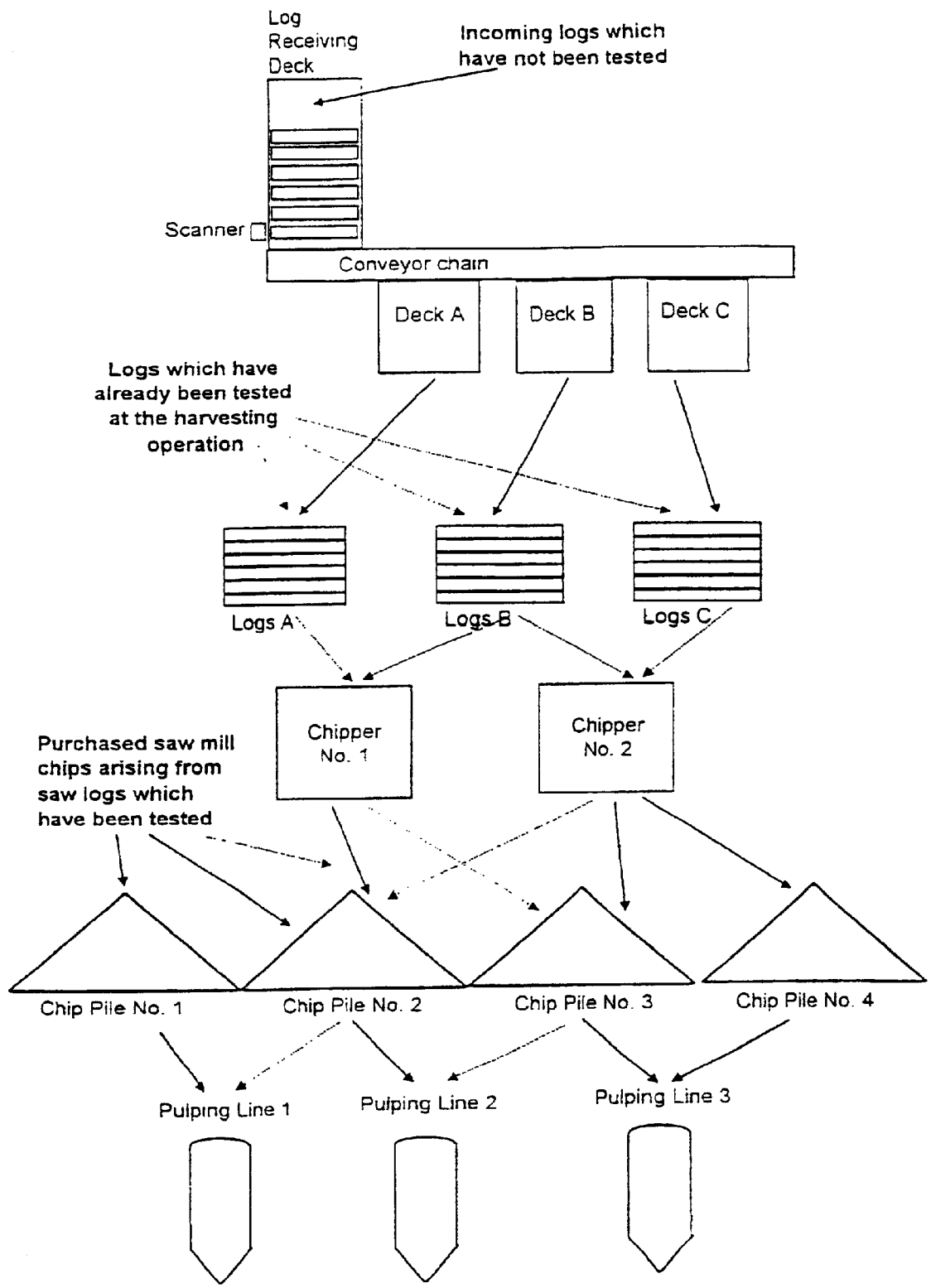
FIG. 2 is a schematic representation of potential commercial application of the method of the invention at a pulp mill.

FIG. 2 further illustrates potential commercial application of the method of the invention for pulp log sorting. Acoustic wave testing of whole stems or logs can occur both at the log landing adjacent to harvesting operations and at central log handling facilities, such as the log yard of a pulp mill. Testing at log landings has the advantage that both saw logs and pulp logs can be characterised by sound speed before decisions are made as to which processing facility they are sent to. For example, the sound speed measurement can be used to select saw logs of superior stiffness for sawing into structural grade lumber. However, testing at the log landing will most likely be a manual operation using hand-held devices so may be rather labour intensive.

Pulp logs X which have already been tested for sound speed at the log landing, on arrival at the pulp mill log yard, can be immediately allocated to a particular log pile A, B, C based on this characteristic. Nevertheless, it may be preferable for some processing operations to have automated sound speed measurement at a central stem or log handling facility. The pulp mill log yard would be one such facility in which large numbers of logs can be tested and segregated into different log piles according to sound speed.

All logs arriving at the central log handling facility can be received on a landing which automatically conveys them into a stress wave testing centre 10. Automatic acoustic testing could involve equipment which could grip each log, measure its length, sense the position of one or both log ends, and then automatically apply the acoustic wave transit time measurement. The log would then be "bucked" off the main chain conveyor 11 onto one of several decks 12 according to the measured velocity of sound. Logs with speeds within given ranges would be classified according to the pulp mill's product requirements. Log stackers would then move the logs from each landing into separate log piles A, B, C, each representing a separate sound speed class.

The logs would then be processed in chippers 13, 14. Chipping operations at pulp mills can typically feed chips into several different chip piles 15, 16, 17 18. Chips are then reclaimed off these piles and fed into the various pulp mill processing lines 19, 20, 21. Different pulping lines may be dedicated to different product types or a pulping line may swing between different pulp grades using a campaigning strategy.

In either case, chips can normally be fed into a pulping line from any of the different chip piles.

Pulp mills also receive a large amount of their wood supply in the form of wood chips Z, which are produced at saw mills from the waste slabwood taken from the outside of saw logs. If a saw log has been tested for sound speed before sawing, such that logs of a given sound speed class can be sawn as a batch, then the chips arising from the slabwood would already be characterised as to their end-use suitability for processing into pulp. On arrival at the pulp null, such "sound-speed characterised" saw mill chips 22 could be blended into the appropriate chip pile 15, 16, 17, 18.

It will be appreciated that FIG. 2 is simply one example of a possible pulp log sorting process involving the method of the present invention, and other examples might include any number of categories of logs, chippers, chip pile categories and pulp line.

The method of the invention may be used to select wood for the production of kraft pulp, for other types of pulping such as semi-chemical, chemical, chemi-mechanical, and mechanical pulping, and also for use in the selection of wood for other wood-fibre-based applications such as fibre board production including the production of medium density fibre board in particular.

The method of the invention is further illustrated by the following examples:

EXAMPLE 1

250 logs of radiata pine taken randomly from a lumber mill were peeled to expose the corewood at the centre of the log. Each peeler core was tested for speed of sound (using a Metriguard Model 239A stress wave timer), before samples from each log were taken for subsequent measurement of key pulp and paper properties.

The peeler cores, and their corresponding discs removed for pulping, were divided into classes with respect to sound speed. The sound speeds varied from 1.44 to $4.16 \times 10^3$ m/s, and the population of peeler cores was divided into classes at $0.157 \times 10^3$ m/s intervals, giving a total of 18 sound classes, each containing between 2 and 34 peeler core samples.

The samples for each sound speed class were grouped, chipped and pulped. The half scale Kappa number of each pulp was tested to ensure that it had been delignified sufficiently, and if so handsheets were formed for measurement of WZST strength, internal tearing resistance and tensile strength characteristics. In addition fibre length measurements were taken using a Kajaani FS200 fibre analyser. Length weighted average fibre length (LWFL) and weight weighted average fibre length (WWFL) were calculated.

The average velocity of sound and the number of peeler cores in each class are shown in Table 2. The distribution for the 18 sound classes was within sensing distance of normal.

Large variations in both average fibre length and pulp strength were observed across the 18 sound classes of wood. This was an unexpected and surprising result given that the sample population of 250 samples all contained only corewood. The average fibre length ranged from 1.77 to 2.78 mm LWFL, whilst the average pulp strength ranged from 9.92 to 16.54 km WZST.

Figure 3:
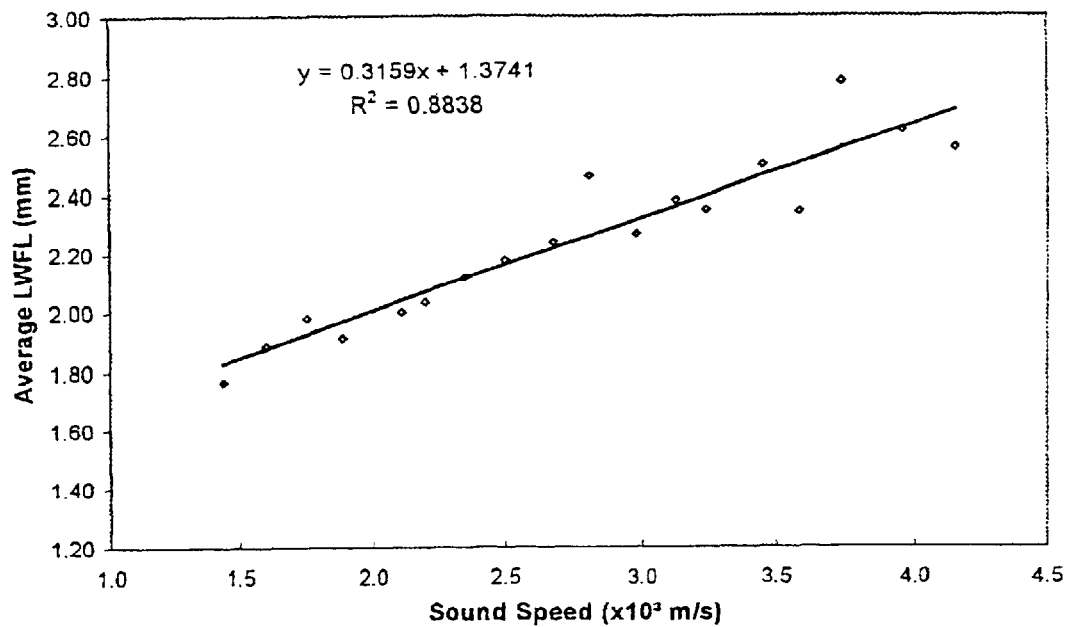
FIG. 3 is a graph of average length weighted average fibre length (LWFL) against sound speed results from the trial described in example 1.
Figure 4:
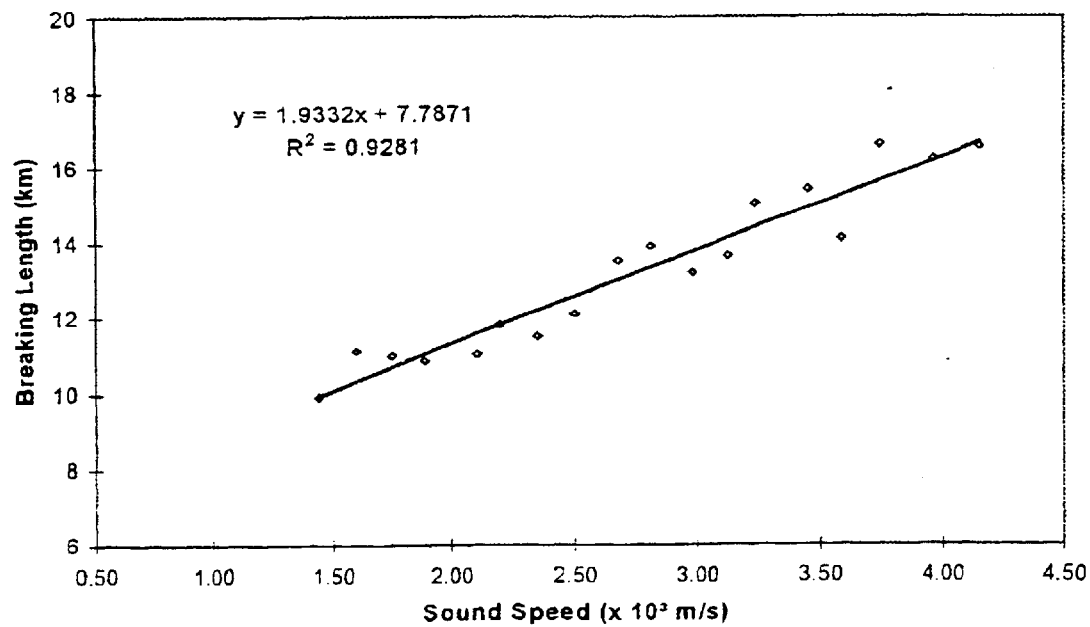
FIG. 4 is a graph of Wet Zero Span Tensile (WZST strength) versus sound speed results from the trial described in example 1.
Figure 5:
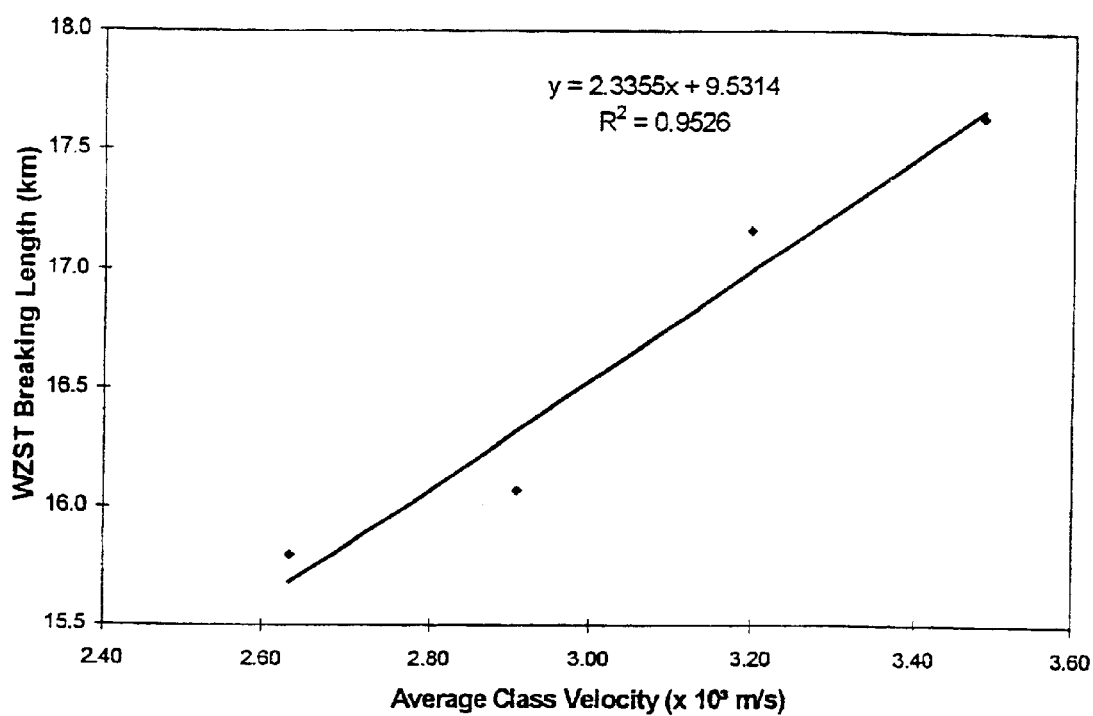
FIG. 5 is a graph of WZST strength versus average log group sound speed results from the trial described in example 2.
Figure 6:
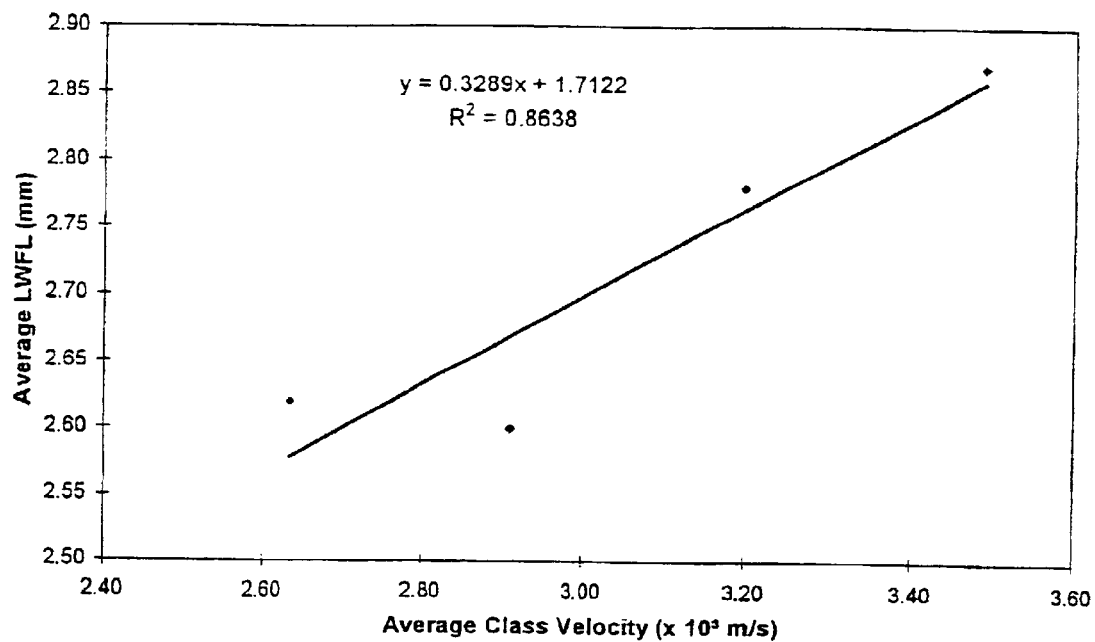
FIG. 6 is a graph of LWFL versus average log group sound speed results from the trial described in example 2.
Figure 7:
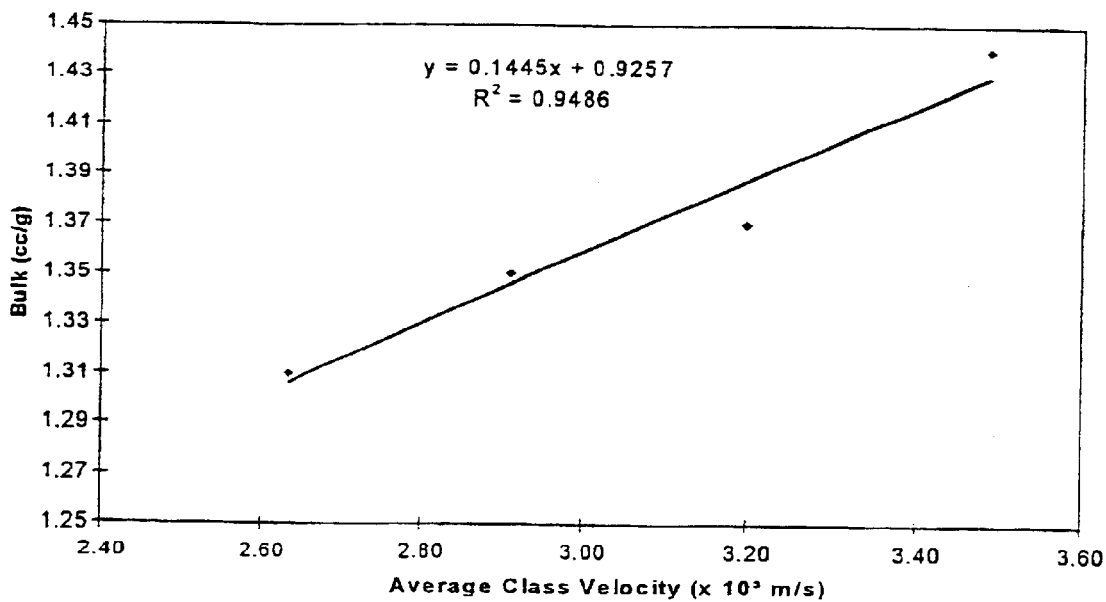
FIG. 7 is a graph of handsheet bulk versus average log group sound speed measurement results from the trial described in example 2.
Figure 8:
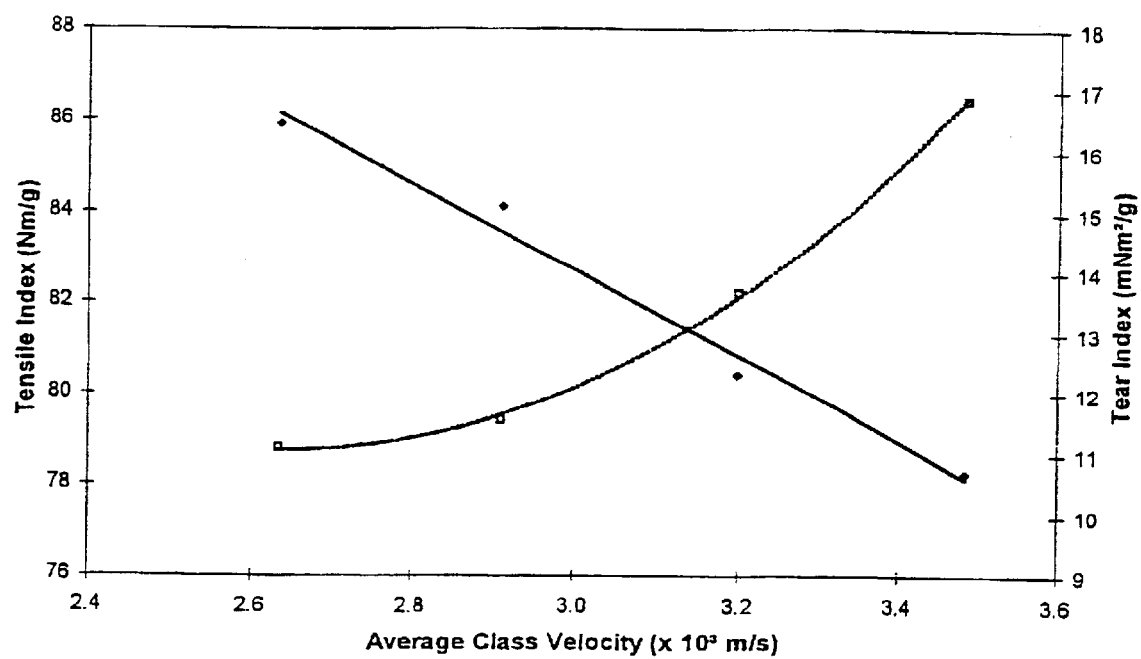
FIG. 8 is a graph of handsheet Tensile and Tear Indices versus average log group sound speed measurement results from the trial described in example 2.

A strong correlation was identified between sound speed and fibre length ($R^2$ of 89%) and sound speed vs WZST strength ($R^2$ of 93%) as shown in FIGS. 3 and 4 which show LWFL versus sound speed for each of the 18 sound classes and WZST breaking length versus average sound speed for each of the 18 sound classes, respectively.

The strong correlation between average LWFL and sound speed is remarkable, as is the distinct difference between the fibre length distributions for the different sound classes. For example, the distribution for class 16 (from 3.7 to less than $3.86 \times 10^3$ m/s) would normally be associated with high density slabwood chips and not corewood. In contrast classes 1 and 2 (1.35 to less than $1.66 \times 10^3$ m/s) contained very short fibres, even shorter than would normally be associated with corewood. Previously available information, based on basic density information, had indicated that corewood samples of the type employed in this trial should have been reasonably homogeneous in relation to fibre quality. These results clearly show this not to be the case. Similarly, with regard to WZST strengths, strengths greater than 15 km are normally associated with high density, slabwood chips whereas some of the core samples had WZST strengths as high as 16.5 km.

TABLE 2

Sound Class Data

| Class Limits ($\times 10^3$ m/s) | Average Velocity ($\times 10^3$ m/s) | Number of Cores | Cumulative Percentage |
|---|---|---|---|
| 1.35–1.50 | 1.44 | 2 | 0.8 |
| 1.50–1.66 | 1.60 | 2 | 1.6 |
| 1.66–1.82 | 1.75 | 12 | 6.4 |
| 1.82–1.97 | 1.89 | 16 | 12.8 |
| 1.97–2.13 | 2.11 | 15 | 18.8 |
| 2.13–2.29 | 2.20 | 24 | 28.4 |
| 2.29–2.44 | 2.35 | 22 | 37.2 |
| 2.44–2.60 | 2.50 | 29 | 48.8 |
| 2.60–2.76 | 2.68 | 34 | 62.4 |
| 2.76–2.92 | 2.81 | 21 | 70.8 |
| 2.92–3.07 | 2.98 | 23 | 80.0 |
| 3.07–3.23 | 3.13 | 10 | 84.0 |
| 3.23–3.39 | 3.24 | 15 | 90.0 |
| 3.39–3.54 | 3.45 | 10 | 94.0 |
| 3.54–3.70 | 3.59 | 5 | 96.0 |
| 3.70–3.86 | 3.74 | 4 | 97.6 |
| 3.86–4.01 | 3.96 | 4 | 99.2 |
| 4.01–4.17 | 4.16 | 2 | 100 |

Example 2

250 logs of 12–42 cm large end diameter were tested for sound speed transmission (using Metriguard Model 239A stress wave timer). The logs were segregated into one of four groups based on sound speed:

Group 1: velocity<2.72 km/s

Group 2: $2.72 \leq$ velocity<3.07 km/s

Group 3: $3.07 \leq$ velocity<3.40 km/s

Group 4: velocity$\geq 3.40$

The logs in each group were then chipped with a composite sample collected as the chips exited the chipping plant, so that four composite samples were collected, representative of the chips generated from each sound speed group.

Each chip sample was screened to remove oversized chips and fines and then kraft pulped under standard conditions (16% Effective Alkali, 30% Sulphidity, 1 hour time-to-temperature, 1 hour at 170° C.) to approximately 26 kappa number. The pulps were washed and screened to remove shives, and then evaluated for properties.

LWFL was measured with a Kajaani FS200 fibre analyser. Pulps were refined in the PFI Mill for 1000 revolutions and standard handsheets prepared according to appropriate Appita standard methods. WZST strength was measured with a Pulmac TS100 Tensile Tester and other handsheet properties were measured according to Appita standards. The basic density of the chips was also measured according to the Appita standard.

The characteristics of the four sound classes are shown in Table 3.

TABLE 3

Characteristics of four sound classes

| | Wood Chip Properties | | Pulp Properties | | Handsheet Properties at 1000 PFI Revolutions | | |
|---|---|---|---|---|---|---|---|
| | | Average | | | | Tensile | |
| Group | % Dry Content | Basic Density (kg/m³) | Group Velocity (km/s) | WZST (km) | LWFL (mm) | Bulk (cm³/g) | Index (Nm/g) | Tear Index (mNm²/g) |
| 1 | 37.8 | 374 | 2.63 | 15.80 | 2.62 | 1.31 | 85.92 | 11.10 |
| 2 | 39.6 | 379 | 2.91 | 16.07 | 2.60 | 1.35 | 84.14 | 11.56 |
| 3 | 41.7 | 389 | 3.20 | 17.17 | 2.78 | 1.37 | 80.43 | 13.67 |
| 4 | 46.3 | 428 | 3.49 | 17.64 | 2.87 | 1.44 | 78.27 | 16.86 |

The relationship between pulp properties and average class sound speed are shown in FIGS. 5 to 8, which show respectively the WZST strength, LWFL, handsheet bulk, and handsheet Tensile and Tear Indices versus average log group sound speed measurement for the four sound classes.

It is evident from the data that the pulps generated from the four log groups are distinctly different in properties. Hence, segregation of the logs has resulted in a useful classification according to their fibre properties. Surprisingly, log groups 1–3 have relatively low basic density, yet relatively high fibre lengths and pulp strengths. This further indicates the superior predictive ability of sound speed over basic density as an indicator of fibre properties.

Example 3

Eighty trees were felled from a 27 year old radiata pine plantation on the Mamaku Plateau in the Central North Island of New Zealand. Each stem was cut into four logs of 4.2 m length, yielding approximately 300 logs which were then tested for sound speed transmission using Metriguard Model 239A Stress Wave Timer. The logs were segregated into four groups according to their position within the stem. The range of sound speeds within each group were normally distributed with means and ranges as follows:

| | Mean velocity (km/s) | Range (km/s) |
|---|---|---|
| Butt | 2.55 | 1.98–3.21 |
| Second | 2.81 | 2.22–3.73 |
| Third | 2.78 | 2.29–3.63 |
| Top | 2.69 | 2.21–3.34 |

Within each log group, four sets of 5 logs were selected—the slowest 5 logs, 5 logs at the 33$^{rd}$ percentile of speed, 5 logs at the 66$^{th}$ percentile of speed, and the 5 fastest logs (the sub groups were designated I–IV respectively). Thus 20 individual logs were selected for each log group (Butt, Second, Third, and Top) giving 80 logs in total.

The logs were then cant-sawn into lumber according to a standard pattern, with the identification of each log tracked through the sawmill. The outerwood slabs from each log were passed through a chipper and a composite chip sample was collected.

The chip samples were combined into a single composite sample for each sub-group of 5 logs (I, II, III and IV) for each log type (Butt, Second, Third, and Top). Thus, 16 composite chip samples were obtained, 4 for each log type.

Each chip sample was screened to remove oversized chips and fines and then kraft pulped under standard conditions (16% Effective Alkali, 30% Sulphidity, 1 hour time-to-temperature, 1 hour at 170° C.) to approximately 26 kappa number. The pulps were washed and screened to remove shives, and then evaluated for properties.

LWFL was measured with a Kajaani FS200 fibre analyser. Pulps were refined in the PFI Mill for 1000 revolutions and standard handsheets prepared according to appropriate Appita standard methods. WZST strength was measured with a Pulmac TS100 Tensile Tester.

The average sound speed of each log group is shown in Table 4 along with the properties of the pulps derived from the outerwood chip samples.

TABLE 4

Log class sound speeds and the properties of the derived pulps

| Sample ID | Average Sound Speed (km/s) | Fibre Length (LWFL, mm) | WZST Strength (km) |
|---|---|---|---|
| Butt Logs | | | |
| Group I | 2.08 | 2.72 | 15.40 |
| Group II | 2.45 | 2.90 | 16.76 |
| Group III | 2.65 | 2.72 | 16.60 |
| Group IV | 3.06 | 2.82 | 17.52 |
| Second Logs | | | |
| Group I | 2.28 | 2.80 | 16.01 |
| Group II | 2.69 | 2.93 | 16.85 |
| Group III | 2.93 | 3.00 | 18.13 |
| Group IV | 3.39 | 3.10 | 19.03 |
| Third Logs | | | |
| Group I | 2.34 | 2.66 | 15.91 |
| Group II | 2.69 | 2.93 | 17.33 |
| Group III | 2.85 | 2.83 | 17.68 |
| Group IV | 3.35 | 3.09 | 18.59 |
| Top Logs | | | |
| Group I | 2.29 | 2.49 | 14.19 |
| Group II | 2.61 | 2.78 | 17.02 |
| Group III | 2.79 | 2.65 | 17.57 |
| Group IV | 3.13 | 2.94 | 18.57 |

Figure 9:
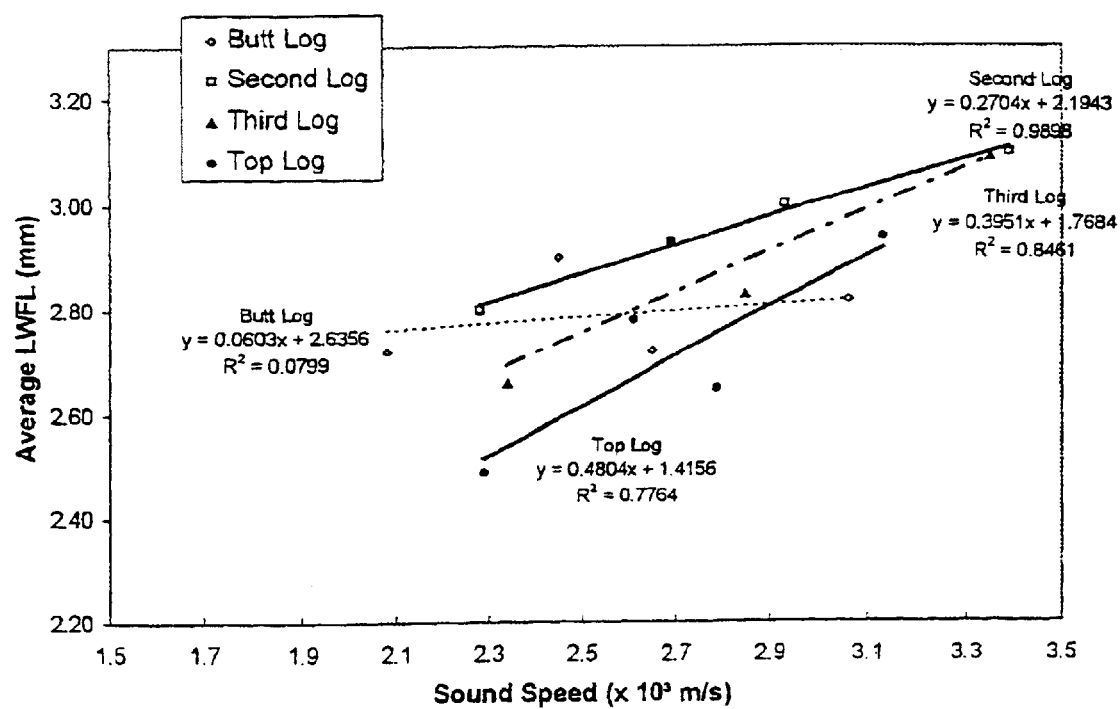
FIG. 9 is a graph of average pulp fibre length versus log sound speed for log type results from the trial described in example 3.
Figure 10:
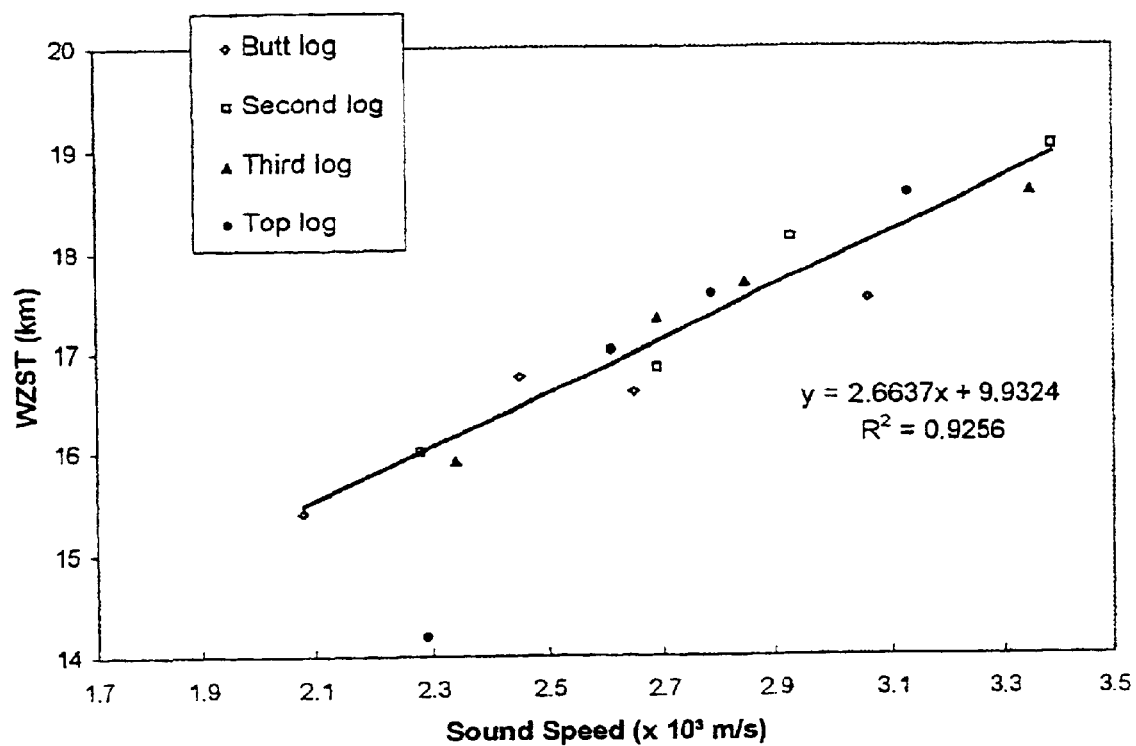
FIG. 10 is a graph of pulp (WZST) strength versus log sound speed by log type results from the trial described in example 3.

FIGS. 9 and 10 respectively plot LWFL and WZST strength against average log group sound speed.

All the WZST strength data fall on the same trend line with sound speed, regardless of log position in the tree. This is a useful observation, since outerwood from sawmills could be segregated for pulp processing (based on expected pulp strength) on the basis of the whole log sound speed. This would only require the sawmill to saw logs in batches based on sound speed, so that outerwood chips could be conveniently segregated.

The foregoing demonstrates that for radiata pine pulp wood of varying quality the method of the invention may closely determine fibre properties of pulps including fibre length, pulp strength, and paper properties. It is well known that pulp and paper properties relate to fibre dimensions for pulps from hardwood species such as eucalyptus.

The foregoing describes the invention including preferred forms thereof. Alterations and modifications as will be obvious to those skilled in the art are intended to be incorporated within the scope hereof.

What is claimed is:

1. Apparatus for predictively assessing a measure of the average fibre length of wood fibre or wood pulp to be produced from a solid wood member, comprising:
    a sensor capable of detecting the velocity of a sound wave through a solid wood member along the length thereof; and
    a computer comprising stored information on fibre length of produced wood fibre or wood pulp versus sound velocity through wood and arranged to determine a measure of average fibre length for the wood fibre or wood pulp to be determined by reference to said stored information on fibre length versus detected velocity through the solid wood member.

2. Apparatus for predictively assessing a measure of average fibre length of wood fibre or wood pulp to be produced from a solid wood member, comprising:
    a sensor capable of detecting both an original and a reflected sound wave in a solid wood member along the length thereof; and
    a computer comprising stored information on fibre length of produced wood fibre or wood pulp versus sound velocity through wood and arranged to determine a measure of average fibre length for the wood fibre or wood pulp to be produced by reference to said stored information on fibre length versus detected velocity through the solid wood member.

3. Apparatus according to claim 1 arranged to determine a measure of strength of pulp to be produced from a solid wood member.

4. Apparatus for predictively assessing at least one characteristic of wood fibre or wood pulp to be produced from a solid wood member, wherein the characteristic is average fibre length, comprising:
    a sensor capable of detecting both an original and a reflected sound wave in a solid wood member along the length thereof; and
    a computer comprising stored information on fibre characteristics versus sound velocity through wood and arranged to determine a measure of the average fibre length of wood fibre to be produced from the solid wood member by reference to said stored information on the average fibre length versus detected sound velocity through the solid wood member.

* * * * *